(12) United States Patent
Lu

(10) Patent No.: US 8,353,770 B2
(45) Date of Patent: Jan. 15, 2013

(54) MOBILE SOCIAL FITNESS NETWORKED GAME

(76) Inventor: Fletcher Lu, Oshawa (CA)

(*) Notice: Subject to any disclaimer, the term of this patent is extended or adjusted under 35 U.S.C. 154(b) by 4 days.

(21) Appl. No.: 13/022,051

(22) Filed: Feb. 7, 2011

(65) Prior Publication Data

US 2011/0195780 A1 Aug. 11, 2011

Related U.S. Application Data

(60) Provisional application No. 61/301,681, filed on Feb. 5, 2010.

(51) Int. Cl.
*A63F 9/24* (2006.01)
(52) U.S. Cl. ........................................................ 463/39
(58) Field of Classification Search .......... 434/247–255; 463/42, 39
See application file for complete search history.

(56) References Cited

U.S. PATENT DOCUMENTS

| | | | | |
|---|---|---|---|---|
| 6,210,272 B1* | 4/2001 | Brown | | 463/1 |
| 2002/0090985 A1* | 7/2002 | Tochner et al. | | 463/1 |
| 2005/0021292 A1* | 1/2005 | Vock et al. | | 702/182 |
| 2006/0089840 A1* | 4/2006 | May | | 705/1 |
| 2008/0015089 A1* | 1/2008 | Hurwitz et al. | | 482/8 |

* cited by examiner

*Primary Examiner* — Omkar Deodhar
(74) *Attorney, Agent, or Firm* — Quarles & Brady LLP; Dale Regelman; Nikia L. Gray

(57) ABSTRACT

A mobile fitness device and method of use are presented. The mobile fitness device includes a controller having a processor and a non-transitory computer readable medium in communication with the processor, wherein the non-transitory computer readable medium has instructions encoded thereon to record performance data that is based upon a performance of a physical activity by a user of the mobile fitness device and to transmit a communication, including the performance data, to a social network or to others for fitness, socialization, and potential game playing.

15 Claims, 5 Drawing Sheets

MOBILE SOCIAL FITNESS NETWORKED GAME

CROSS REFERENCE TO RELATED APPLICATIONS

This application claims the benefit of and priority from U.S. Provisional Patent Application No. 61/301,681 filed on Feb. 5, 2010, entitled "Mobile Social Fitness Networked Game," the disclosure of which is hereby incorporated by reference in its entirety.

BACKGROUND

The health benefits of a lifelong practice of regular physical activity are well known and documented. Most significantly, regular physical activity of moderate to vigorous intensity is known to greatly reduce the risk of cardiovascular disease, developing type II diabetes, hypertension, and colon cancer. Physical activity is also known to enhance mental health, foster healthy muscles, bones, and joints, and to help maintain and preserve independence in older adults.

However, the evidence regarding what helps individuals incorporate physical activity into their lives is less clear. Programs have been put in place to provide physical education classes in schools, health programs at worksites, and counseling by health care providers. Yet, obesity continues to be cited as a major health issue in industrialized countries. In the United States in particular obesity rates are among the highest in the world with some reports estimating that as much as thirty percent (30%) of all adults are obese. Thus, what is needed is a means to help individuals incorporate regular physical activity into their life.

SUMMARY

In certain embodiments a mobile fitness device is provided. The mobile fitness device includes a controller having a processor and a non-transitory computer readable medium in communication with the processor, wherein the non-transitory computer readable medium has instructions encoded thereon to record performance data that is based upon a performance of a physical activity by a user of the mobile fitness device and to transmit a communication including the performance data.

In other embodiments a system is presented. The system comprises a mobile fitness device having a controller, where the controller has a first processor and a first non-transitory computer readable medium in communication with the first processor, where the first non-transitory computer readable medium has instructions encoded thereon to record performance data that is based upon a performance of a physical activity by a user of the mobile fitness device and to transmit a communication comprising the performance data. The system further includes a server having a second processor and a second non-transitory computer readable medium in communication with the second processor, where the second non-transitory computer readable medium has instructions encoded thereon to do at least one of: determining a score based upon the performance data and generating a statistic based upon the performance data.

In yet other embodiments a method is presented. The method includes providing a mobile fitness device having a controller, where the controller has a processor and a non-transitory computer readable medium in communication with the processor, where the non-transitory computer readable medium has instructions encoded thereon to record performance data that is based upon a performance of a physical activity by a user of the mobile fitness device and to transmit a communication comprising the performance data. The method further includes generating, using the mobile fitness device, the performance data and transmitting, using the mobile fitness device, the communication.

In yet another embodiment a method is provided. The method includes providing a server having a processor and a non-transitory computer readable medium in communication with the processor, where the non-transitory computer readable medium has instructions encoded thereon to do at least one of: determining a score based upon performance data, where the performance data is based upon a performance of a physical activity by a user of a mobile fitness device, and generating a statistic based upon the performance data. The method further includes receiving, using the server, a first communication having the performance data and determining, using the server, at least one of: a score based upon the performance data and a statistic based upon the performance data.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

Figure 1A:
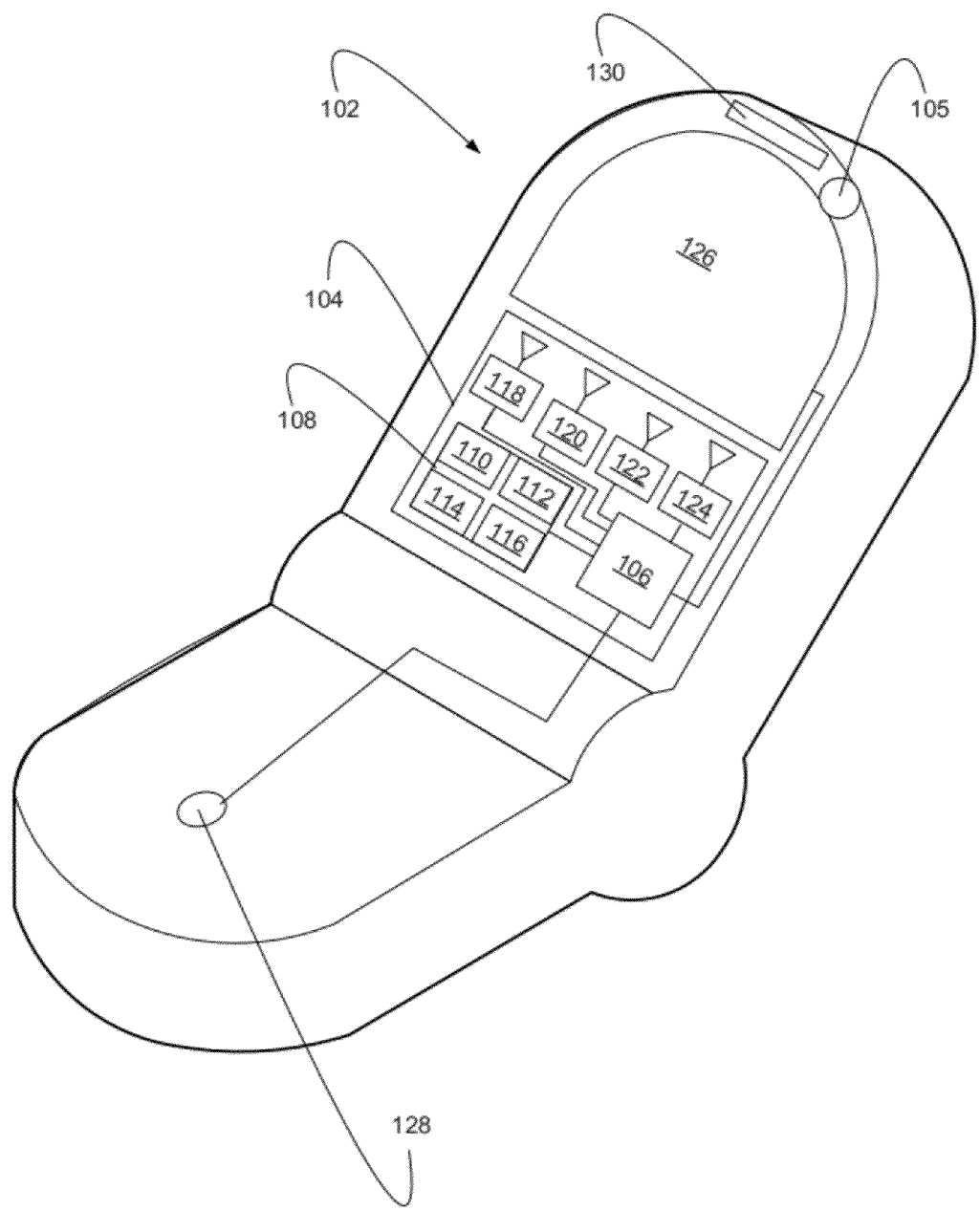
FIG. 1A is a block diagram of an embodiment of Applicant's mobile communication device for use with Applicant's social network game.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Many of the functional units described in this specification have been labeled as modules (e.g., modules 118, 120, 122, and 124) in order to more particularly emphasize their implementation independence. For example, a module (e.g., modules 118, 120, 122, and 124) may be implemented as a hardware circuit comprising custom VLSI circuits or gate arrays, off-the-shelf semiconductors such as logic chips, transistors, or other discrete components. A module (e.g., modules 118, 120, 122, and 124) may also be implemented in programmable hardware devices such as field programmable gate arrays, programmable array logic, programmable logic devices, or the like.

Modules (e.g., modules 118, 120, 122, and 124) may also be implemented in software for execution by various types of processors. An identified module of executable code may, for instance, comprise one or more physical or logical blocks of computer instructions which may, for instance, be organized as an object, procedure, or function. Nevertheless, the executables of an identified module (e.g., modules 118, 120, 122, and 124) need not be physically collocated, but may comprise disparate instructions stored in different locations which, when joined logically together, comprise the module and achieve the stated purpose for the module.

Indeed, a module of executable code (e.g., modules 118, 120, 122, and 124) may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Applicant's invention includes a method and system for a mobile social fitness networking game wherein a mobile communication device, such as a phone, personal digital assistant (PDA), or other such device, detects the location and motion of the user while the user is engaged in an activity and transmits this information to a server for distribution over a social networking site.

In certain embodiments, the server may calculate a score, percent improvement, statistical data, or other information relating to the user's performance for distribution over the social network. The distributed information is then posted on an online profile of the user and/or sent to other users of the social networking site who have been approved by the user. In certain embodiments, the user may approve the posting before it can be seen by or is sent to others. In such embodiments, the user may edit the posting or provide additional comments thereto.

In other embodiments, the location and motion of the user is used by the server to determine an action by the user in a virtual, live action role-playing game (RPG). As will be appreciated by one of ordinary skill in the art, an RPG is a type of game where the players assume the roles of characters in a fictional setting. In live action RPGs, the players perform their character's physical actions. In such an embodiment, the server translates the user's motion and location into an action taken within a virtual world where the user interacts with other users of Applicant's invention to achieve a goal or competes against them, as determined by the rules of the RPG.

As used herein, a "posting" will refer to a posting made by Applicant's server or by a user of Applicant's social network to the network. In certain embodiments, such a posting is made to an online user profile. In other embodiments, the posting is made to an RPG the user is engaged in. In yet other embodiments, the posting is made to a virtual world hosted on Applicant's social network. In certain embodiments, a posting represents information about an activity the user has undertaken. In other embodiments, a posting represents a translation made by a server on Applicant's social network of a user's actions into the action of a character or avatar played by the user.

Turning to FIG. 1A, an embodiment of Applicant's mobile communication device 102 for use with Applicant's social networking game is presented. In the illustrated embodiment of FIG. 1A, device 102 comprises controller 104, optional display 126, optional microphone 128, and optional speaker 130. Controller 104 further comprises processor 106 interconnected via communication links with non-transitory computer readable medium 108, accelerometer module 118, Global Positioning System (GPS) module 120, optional VOIP module 122, and optional "WI-FI" module 124.

One of ordinary skill in the art will appreciate that while device 102 is depicted in FIG. 1A as a cellular telephone and referred to as such throughout a specification, this is meant to be illustrative and not limiting. One of ordinary skill in the art will appreciate that a variety of mobile devices could be used. By way of example and not limitation, device 102 could additionally be a personal organizer, an MP3 player, or a special purpose device specifically designed for use in Applicants' system.

In certain embodiments, non-transitory computer readable medium 108 comprises non-volatile memory. In certain embodiments, non-transitory computer readable medium 108 comprises battery backed up RAM, a magnetic hard disk assembly, an optical disk assembly, and/or electronic memory. By "electronic memory," Applicant means a PROM, EPROM, EEPROM, SMARTMEDIA, FLASHMEDIA, and the like.

Accelerometer module 118 comprises an accelerometer and a dynamic monitoring system for measuring and recording data from the accelerometer. As will be appreciated by one of ordinary skill in the art, an accelerometer measures the acceleration of motion of a structure. The accelerometer may be any type of accelerometer, such as and without limitation a piezo-electric, piezo-resistance, micro electro-mechanical systems (MEMS), bulk micromachined piezo resistive, bulk micromachined capacitive, strain gauge, null-balance, resonance, magnetic induction, optical, thermal, or any other type of accelerometer.

As those skilled in the art will appreciate, GPS module 120 comprises a wireless device that receives a plurality of signals from a plurality of GPS satellites, and determines a location for the GPS device using that plurality of signals.

Figure 1B:
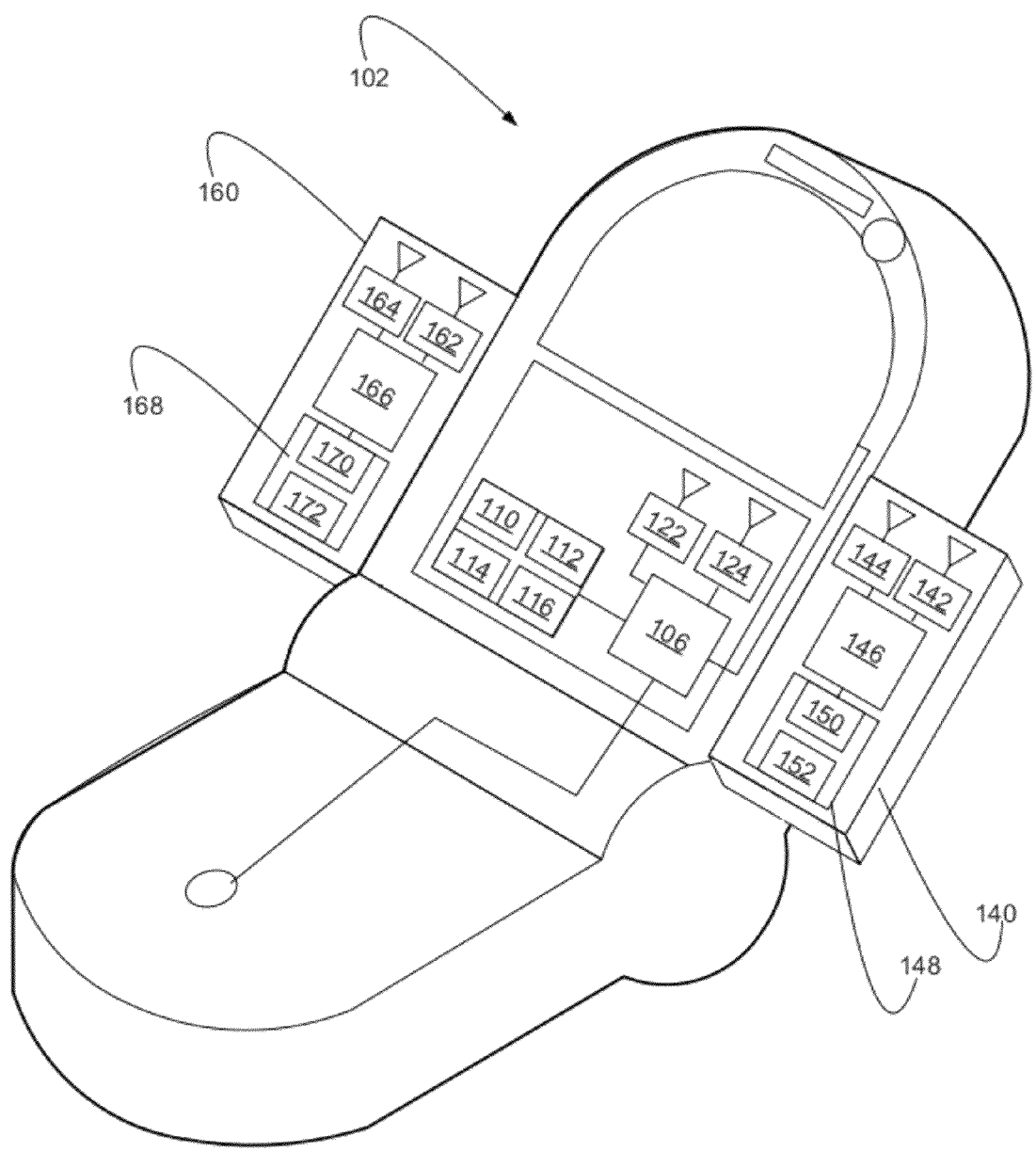
FIG. 1B is a block diagram of an alternative embodiment of Applicant's mobile communication device having external accelerometer and GPS devices for use with Applicant's social network game.

In the illustrated embodiment of FIG. 1A, accelerometer module 118 and GPS module 120 are internal to device 102. In other such embodiments, accelerometer module 118 and GPS module 120 may be external to device 102 as an attachments thereto. FIG. 1B illustrates an embodiment where accelerometer device 160 and GPS device 140 are externally located to device 102.

In the illustrated embodiment of FIG. 1B, Externally attached GPS device 140 comprises processor 146 interconnected via communication links to memory 148 and GPS module 142. Optionally, processor 146 may also be interconnected via a communication link with wireless communication module 144. In such embodiments, GPS device 140 may provide data regarding it's location wirelessly to device 102. In such embodiment, GPS device 140 may not be in physical contact with device 102 but may instead be in proximity to device 102.

Accelerometer device 160 comprises processor 166 interconnected via communication links to memory 168 and accelerometer module 162. Optionally, processor 166 may also be interconnected via a communication link with wireless communication module 164. In such embodiments, accelerometer device 160 may provide data regarding the user's movement wirelessly to device 102. In such embodiment, accelerometer device 160 may not be in physical contact with device 102 but may instead be in proximity to device 102.

In other embodiments, GPS device 140 and/or accelerometer device 160 may be interconnected with device 102 by a communication link with a data input/output port of device 102 (not shown), wherein the port comprises, by way of example and not limitation, a FireWire port, USB port, or any other type of port used to interconnect a wireless communication device with an external attachment.

As will be appreciated by one of ordinary skill in the art, the embodiment of FIG. 1B is particularly useful where a user's cell phone or other portable communication device lacks an internal accelerometer and/or GPS module. One of ordinary skill in the art will further realize that in certain embodiments a user's cell phone may have an internal GPS device but lack an accelerometer, or may have an internal accelerometer but lack a GPS module. In such embodiments, the user would only need to use a single attachment to utilize Applicant's social networking game. Alternatively, for a particular activity, the GPS module may not be important, such as by way of example and not limitation, an aerobic workout or strength training. In such embodiments, a user would not need to use the GPS attachment. For other activities, such as running, an accelerometer may not be required and thus a user may choose not to use an externally attached accelerometer.

In certain embodiments, even where device 102 has internal GPS module 120 and accelerometer module 118, a user may still prefer to utilize external GPS and accelerometer devices. Such situations may include where it is preferable not to have device 102 located on the user's body but where the user will remain in proximity to device 102 such that wireless communication is possible. For example, most cell phones and similar wireless communications devices are not waterproof. Thus, for swimming and other similar activities, a user could leave device 102 near the pool or other body of water and take waterproof versions of GPS device 140 and/or accelerometer device 160 into the water with her/him. In such situations, GPS device 140 and accelerometer device 160 may wirelessly transmit information to device 102 for transmission to a server within Applicant's social network while user 202 is in the water, thereby eliminating risk of damage to device 102. Alternatively, GPS device 140 and accelerometer device 160 may store data about the user's performance in memory 148 and 168, respectively, and then transfer the data to device 102 when GPS device 140 and accelerometer device 160 are connected to device 102 via a communication port on device 102 or are within wireless communication range of device 102.

Turning back to FIG. 1A, optional VOIP module 122 implements a Voice over Internet Protocol (VoIP). VoIP is a general term for a family of transmission technologies for delivery of voice communications over IP networks such as the Internet or other packet-switched networks. Internet telephony includes communications services, such as and without limitation voice, facsimile, and/or voice-messaging applications, that are transported via the Internet, rather than the public switched telephone network (PSTN).

Optional WI-FI module 124 comprises a wireless network communication module comprising a wireless network permitting communication with one or more external computers or programmable devices in a network or with point-to-point communications. In certain embodiments, WI-FI module 124 implements one or more of the embodiments of IEEE Specification 802.11 (collectively the "IEEE Specification"). As those skilled in the art will appreciate, the IEEE Specification comprises a family of specifications developed by the IEEE for wireless LAN technology.

The IEEE Specification specifies an over-the-air interface between a wireless client, such as for example device 102, and a server or between two wireless clients. The IEEE accepted the IEEE Specification in 1997. There are several specifications in the 802.11 family, including (i) specification 802.11 which applies to wireless LANs and provides 1 or 2 Mbps transmission in the 2.4 GHz band using either frequency hopping spread spectrum (FHSS) or direct sequence spread spectrum (DSSS); (ii) specification 802.11a which comprises an extension to 802.11 that applies to wireless LANs and provides up to 54 Mbps in the 5 GHz band using an orthogonal frequency division multiplexing encoding scheme rather than FHSS or DSSS; (iii) specification 802.11b, sometimes referred to as 802.11 High Rate or WI-FI, which comprises an extension to 802.11 that applies to wireless LANS and provides up to about 11 Mbps transmission in the 2.4 GHz band; and/or (iv) specification 802.11g which applies to wireless LANs and provides 20+ Mbps in the 2.4 GHz band.

Processor 106 uses microcode 110 to operate controller 104, WI-FI module 124, VOIP module 122, GPS module 120, accelerometer module 118, display 126, microphone 128, and speaker 130.

In certain embodiments, microphone 128 may be used to record audio files for transmission to a server of Applicant's social network. The recordings may be about the user's own performance or may be designated for another user of Applicant's social network. Alternatively, the recordings may be the user speaking as his/or her character or avatar in an RPG and/or virtual world of Applicant's social network and may be available to other players. In such embodiments, the audio recording is stored on a server of Applicant's social network for downloading by other users.

In certain embodiments, speaker 130 may be used to play commands or instructions transmitted from a server of Applicant's social network to a user. Alternatively, speaker 130 may be used to play audio clips recorded by other users of Applicant's social network.

In certain embodiments, display 126 may be used to display commands, instructions, or other information downloaded from a server of Applicant's social network. In other embodiments, display 126 may be used in combination with an input device (not illustrated) of device 102 to create or edit a posting.

In certain embodiments, device 102 further comprises camera 105. In certain embodiments, camera 105 is a digital camera and is used to take pictures of the user to be posted on Applicant's social network. In other embodiments, camera 105 is a video camera and may be used to take video of the user for display on Applicant's social network. In yet other embodiments, camera 105 is a duel digital video camera capable of taking both digital pictures and video.

Device 102 may be worn on any body part of the user. By way of example and not limitation, device 102 may be worn on the wrist, ankle, waist, forearm, bicep, calve, thigh, chest, head, and/or neck of the user. In certain embodiments, device 102 may be put in the pocket of the user. In other embodiments, device 102 is on a strap or elastic that fits around a body part of the user such as the arm, leg, or neck. In yet other embodiments, device 102 clips onto an article of clothing worn by the user.

Figure 2:
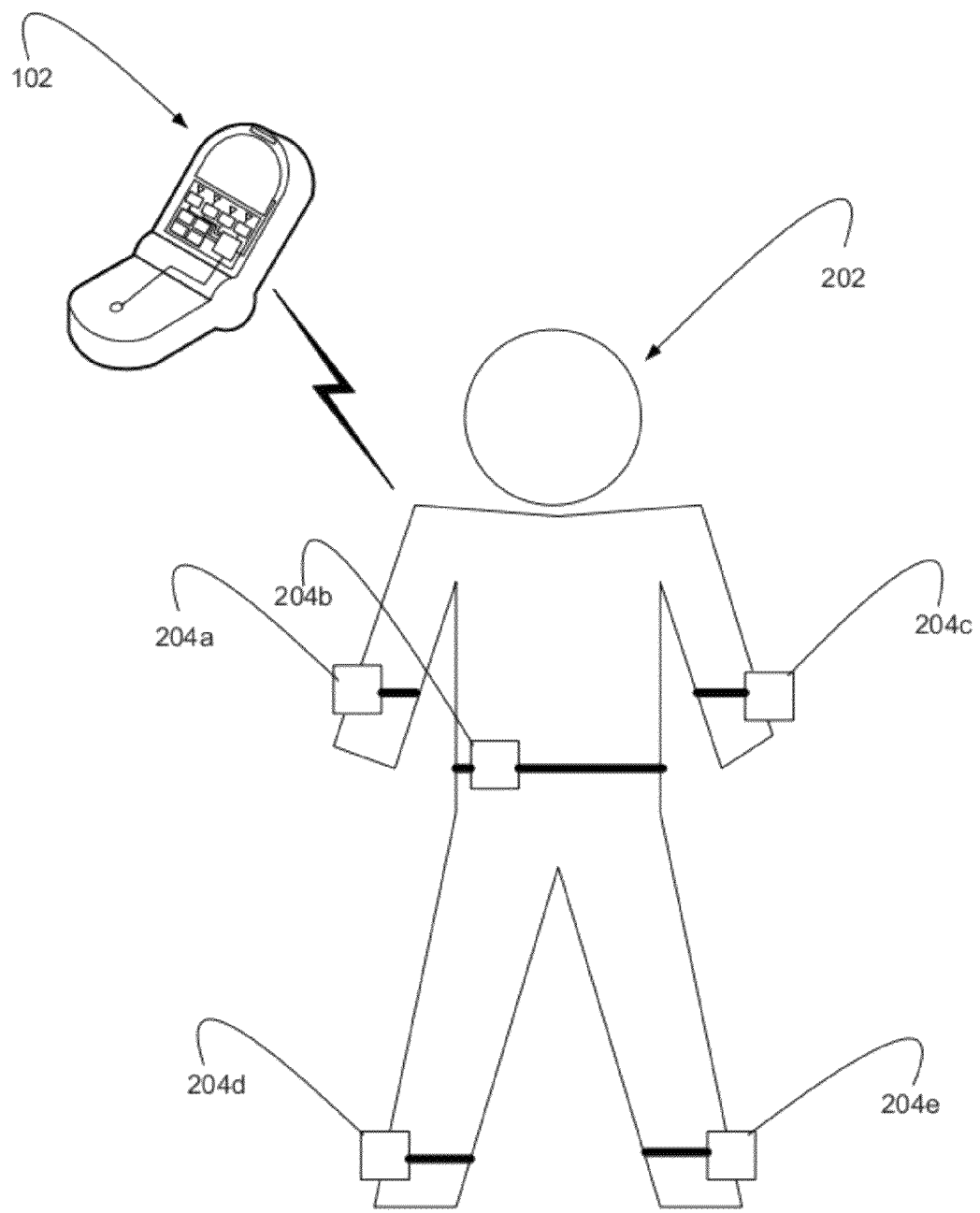
FIG. 2 is a block diagram of a user of Applicant's social networking game wearing additional accelerometer and GPS devices on the user's extremities.

Turning now to FIG. 2, in certain embodiments a user, such as user 202, may wear devices, such as devices 204a-e, each comprising additional accelerometers for activities where it desirable to measure the movement of various body parts relative to one another, such as, and without limitation, dancing or boxing. In such embodiments, devices 204a-e comprise accelerometer devices, such as accelerometer device 160. In such embodiments, devices 204a-e wirelessly transmit information regarding the movement of user 202's body to device 102 for transmission to a server of Applicant's social network.

In other embodiments, devices 204a-e may comprise GPS devices, such as GPS device 140, in addition to or instead of accelerometer devices. Such GPS devices may be used for activities where it is important to know the location of each body part relative to other body parts, such as, and without limitation, figure skating or tai chi.

As can be seen in the illustrated embodiment of FIG. 2, devices 204a-e may be worn around the wrists, ankles, and/or waist of user 202. In certain embodiments, devices 204a-e may be worn around the forearms, biceps, calves, and/or thighs of user 202. In certain embodiments, additional devices 204a-e may be worn around the chest, head, and/or neck of user 202. In certain embodiments, devices 204a-e may be worn around any body part of user 202.

In certain embodiments, the information from devices 204a-e may be used by a server of Applicant's social network to generate a video file or other animation depicting the movement of user 202. Thus, in some such embodiments, other users of Applicant's social network who have access to user 202's profile or are participating in the same RPG and/or virtual world may view and comment on user 202's form or execution of complex movements. Alternatively, such a video file or animation may be presented in a virtual world hosted on Applicant's social network, where user 202's actions are translated into an action taken by a character or avatar played by user 202 within the virtual world. In other such embodiments, the video file or animation is presented on Applicant's social network as an action taken by user 202's online character or avatar within a live-action RPG and/or virtual world hosted on Applicant's social network.

In other embodiments, the information from devices 204a-e may be used by a server of Applicant's social network game to grade user 202's performance or provide feedback to user 202 to improve the execution of certain movements. In other embodiments, the information from devices 204a-e may be used by a server of Applicant's social network game to determine statistical information regarding user 202's performance, such as, and without limitation, the force with which user 202 hit a punching bag or the velocity with which user 202 swung a bat. In other embodiments, the information from devices 202a-e is used by a server of Applicant's social network game to determine a corresponding action taken by user 202's character or avatar within a live-action RPG and/or virtual world.

Figure 3A:
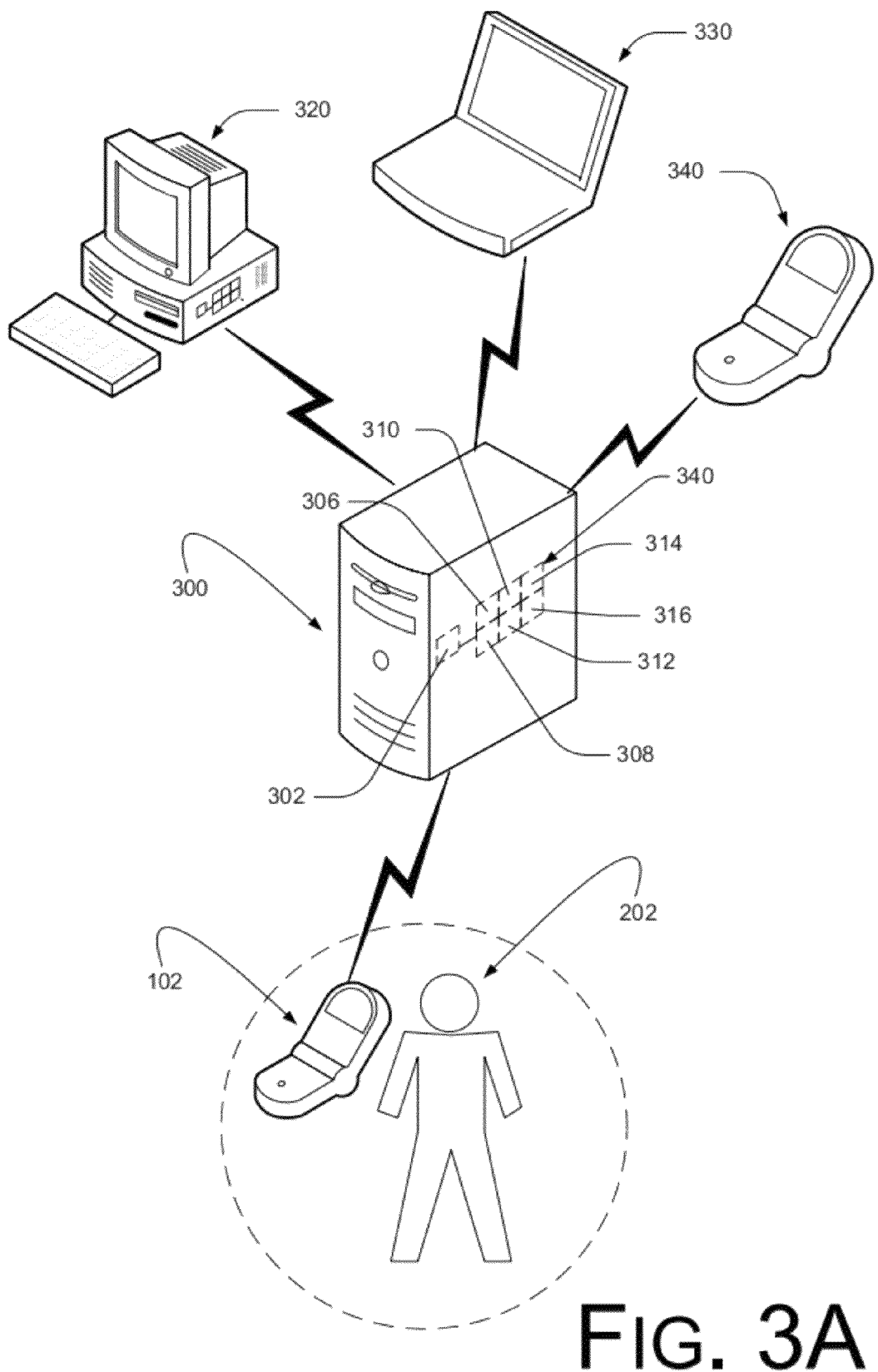
FIG. 3A is a block diagram depicting an exemplary embodiment of a user using the device of FIG. 1A while performing a physical activity, where data regarding the user's performance is transmitted to a server of Applicant's social networking site.

FIG. 3A illustrates an exemplary embodiment of user 202 using device 102 while performing a physical activity. Device 102 collects data regarding user 202s' performance using GPS module 120, and/or accelerometer module 118, and/or GPS device 140, and/or accelerometer device 160. Device 102 may additionally record a sound clip using microphone 128.

The data is transmitted using WI-FI module 124 or VOIP module 122 to server 300. In certain embodiments, the data is transmitted continuously while user 202 is performing the activity. In other embodiments, the data is transmitted at intervals. In yet other embodiments, the data is transmitted at a user determined time.

Server 300 comprises a programmable processor 302 interconnected via a communication link with computer readable medium 340, and computer readable program code 306 encoded in computer readable medium 340.

In the illustrated embodiment of FIG. 3A, server 300 further comprises user information 308 and user performance data 310 encoded in computer readable medium 340. In certain embodiments, user information 308 may include information such as the user 202's weight, height, or age which may be used for example, and not limitation, to generate statistics about user 202, score user 202's performance, or create user 202's online profile. Similarly, user performance data 310 comprises data transmitted from device 102 regarding user 202's current performance as well as previous performances and may be used for example, and not limitation, by server 300 to score user 202's performance, calculate a percent improvement, or generate statistical data. In certain embodiments, user performance data 310 is further used to rank or otherwise compare user 202's performance against other users of Applicant's social network.

In certain embodiments, server 300 further comprises character data 312, RPG data 314, and/or environmental data 316. In such embodiments, character data 312 includes information about a character or avatar user 202 is playing in a live action RPG and/or virtual world, such as the age, species, physical traits, and appearance of the character. In such embodiments, RPG data 314 comprises information concerning the specific RPG user 202 is engaged in, such as the rules of the RPG, information regarding the Game Master (GM) of the RPG where the GM is another user acting as the organizer, arbitrator, and/or officiant of the RPG, other players of the RPG, and similar information. Similarly, environmental data 316 comprises information regarding the physical setting of the virtual world and/or RPG.

In certain embodiments, server 300 uses computer readable program code 306, user information 308, and user performance data 310 to generate postings about user 202's performance. Such postings may be on user 202's profile for viewing by other users of Applicant's social network. In some such embodiments, other users may then comment on the postings or respond by taking actions of their own. By way of example and not limitation the postings may be notices that user 202 is currently engaged in an activity or performed an activity at a certain time, statistical data about user 202's performance, ranking or scoring of user 202's performance, video or other animated clips depicting user 202's performance, or notices that user 202 has just reached a predefined milestone in their performance. Postings may also include information provided by user 202 such as audio recordings, comments, images, or notifications.

In other embodiments, server 300 uses computer readable program code 306, user information 308, and user performance data 310 along with RPG data 314 and environmental data 316 to generate a posting to an RPG or virtual world user 202 is engaged in. Postings may be translations of user 202's actions into actions taken by user 202's character or avatar, scoring of user 202's performance within an RPG, events or actions which occur within the RPG and/or virtual world as a result of user 202's performance, the current status of the RPG, or the next task for user 202 to undertake. In such embodiments, other players in the RPG and/or virtual world may then respond to the action.

In certain embodiments, computer readable medium 340 of server 300 additionally has nominal data stored thereon regarding well known ski trails, running paths, races, etc., which can be used to compare user 202's performance against. Additionally, such information may be used by server 300 to create videos or animations of user 202 or user 202's character or avatar performing some action within the specific environment.

In certain embodiments, computer readable medium 340 also has data regarding professional athletes stored thereon. Such data can be used to allow user 202 to "compete" against a professional athlete. In such embodiments, data regarding the professional athlete may be adjusted to factor in a handicap. Alternatively, data regarding user 202's performance may be adjusted to take into consideration physical traits or skill level.

In certain embodiments, user 202 may approve the postings before they are viewable by other users of Applicant's social network. In other embodiments, user 202 may edit the postings. In yet other embodiments, other users of Applicant's social network may comment on the postings. Such comments may be viewable by only user 202 or may be available for other users of Applicant's social network to view and provide additional comments on.

Figure 3B:
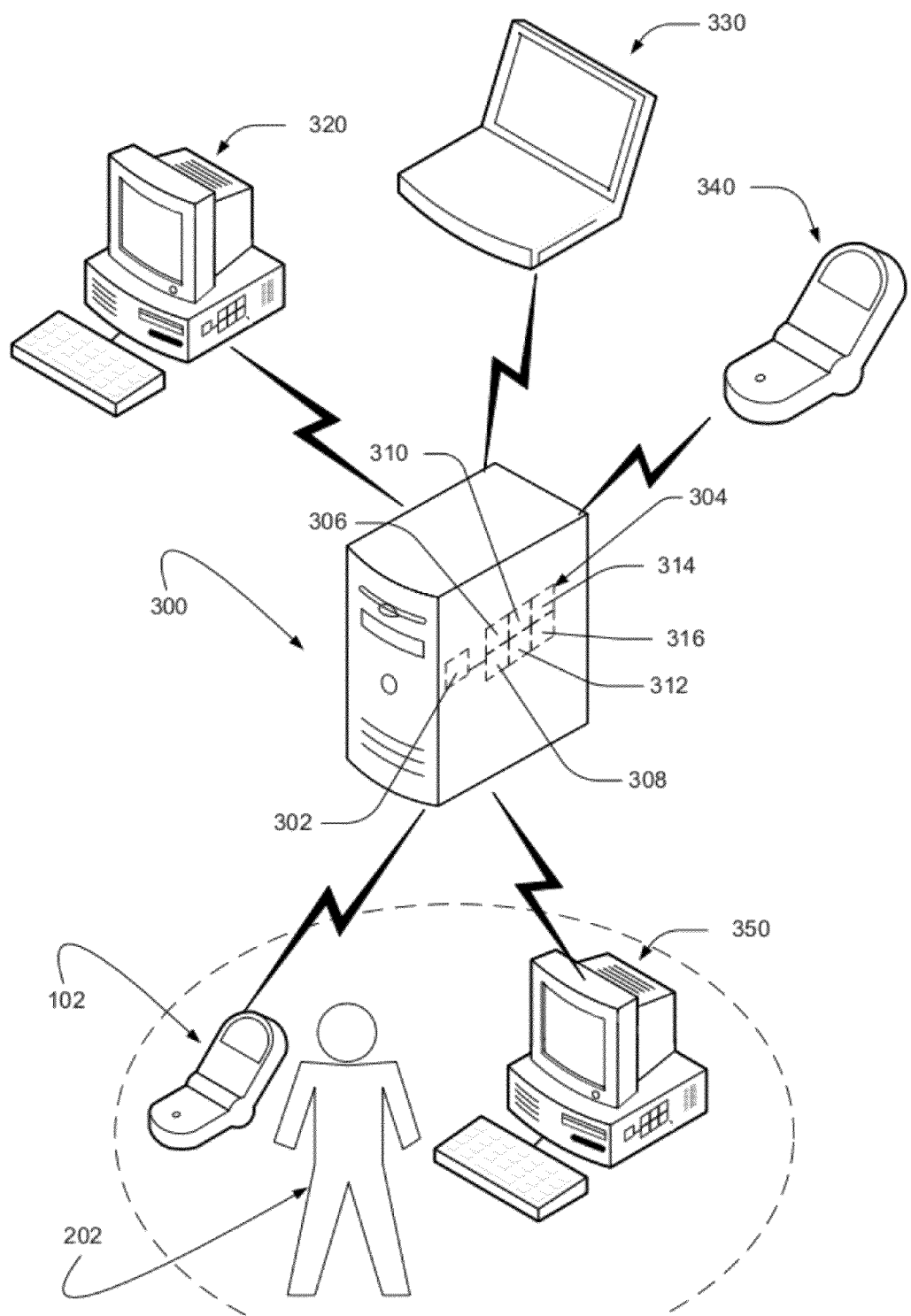
FIG. 3B is a block diagram depicting another exemplary embodiment of a user using the device of FIG. 1A while performing a physical activity, where data regarding the user's performance is transmitted to a server of Applicant's social networking site.

In certain embodiments, user 202 may view and/or edit postings using display 126 of device 102. In other embodiments, user 202 may use a personal computing device, such as personal computing device 350, depicted in FIG. 3B, to view and/or edit postings about user 202's performance.

Postings generated by server 300 are posted to an online profile for user 202, an RPG user 202 is playing, and/or a virtual world user 202 is engaged in. In certain embodiments, copies of the postings may also be sent to other users of Applicant's social network designated by user 202. Alternatively, notices may be sent to such other users notifying them that a new posting has been made regarding user 202. Other users of Applicant's social network may then use personal computing devices, such as personal computing devices 320, 330, and 340, to view the posting and comment on any posting thereon. Personal computing devices 320, 330, and 340 may be any device capable of downloading and rendering a website, such as for example, and not limitation, a personal computer, notebook computer, PDA, cellular phone, BLACKBERRY, or similar device.

The following examples are presented to further illustrate to persons skilled in the art how to make and use the invention. This example is not intended as a limitation, however, upon the scope of the invention, which is defined only by the appended claims.

Example I

By way of example and not limitation, a user may decide to use Applicant's invention while skiing. Prior to leaving their house, the user uses a personal computer to post a message to their online profile saying "Heading to the mountain! Come join me!" At the top of the mountain, the user posts another message to their profile using their cellular phone stating "Going to try Dead Man's Run—Wish me luck!" While skiing down the mountain, the accelerometer and GPS modules within the user's cellular phone transmits data to a server on Applicant's social network regarding the user's position and movements. If the user is wearing additional accelerometer and/or GPS devices, data from these devices is transmitted to the user's phone and then to the server.

Upon receiving data from the user's cellular phone, the server calculates statistical data about the user's performance. Such data may include, by way of comparison and not limitation, the user's average speed, the user's total time to ski down the mountain, the average time for other skiers to ski the same trail, and how much faster the user was this time than on previous times on the same trail. The server may additionally generate an animation of the user's progress down the mountain.

Other users using Applicant's social network can view the postings and reply by posting comments on the user's profile such as "Good Luck!" or "Awesome run!!" for the user to later view.

Example II

By way of example and not limitation, two or more users may use Applicant's invention to compete against one another. In such an embodiment, a first user, user A, may run a specific trail in the morning. Information about user A's performance is sent to a server on Applicant's social network and the server calculates data such as the average speed of user A, how far user A ran, how much faster user A was than previous times user A has run the same course, etc. The server may also generate an animation showing user A's progress and average speed while traversing the course.

User B may then run the same course later in the day. Information about user B's performance is captured by the accelerometer and GPS modules of user B's device 102 and transmitted to a server on Applicant's social network. The server then calculates data regarding user B's performance. In addition, the server may calculate and post information comparing user B's performance with user A's performance, such as who completed the trail faster. Physical information about the users may be used to calculate who has a longer stride or who burned more calories. Additionally, in certain embodiments, one of the users may be given a handicap to account for different physical traits or skill levels. By way of example and not limitation, user A may be ten years older than user B. In such a situation, user A's age may be considered in attributing scores for the user A's performance and user B's performance.

User A's performance and user B's performance may also be scored against a specific professional athlete. In such an embodiment, nominal data about the professional athlete is stored on a server of Applicant's social network. In certain embodiments, user A and/or user B have the option to choose that the professional athlete "play" with a handicap. In such embodiments, data regarding user A's and/or user B's performance may be adjusted to take into consideration the handicap of the professional athlete. In certain embodiments, data regarding user A's performance may be adjusted differently than user B's to take into consideration user A's age or other physical factors. Alternatively, in certain embodiments, data regarding the professional athlete may be adjusted to take into consideration the handicap.

Information about user A's and user B's performances is then posted to their online profiles where they or others can post additional comments.

Example III

By way of example and not limitation, a user may use Applicant's invention while performing pilates. In pilates the accuracy of postures and movements is important and the user may choose to wear additional combination accelerometer/GPS devices on their wrists and ankles such that information regarding the movement of their body can be transmitted to a server on Applicant's social network. The server can use this information to generate feedback for the user on the correct positioning of each movement. In such an embodiment, the feedback may be posted on the user's online profile. Alternatively, the feedback may be provided real time to the user so the user can adjust his or her posture or movement. In such an embodiment, audible instructions may be provided to the user via a speaker on device 102.

Example IV

By way of example and not limitation, a user may use Applicant's invention to engage in a live-action RPG set in a virtual world hosted by Applicant's social network. In such an embodiment, the user may be represented by an avatar the user has selected. The GM of the RPG may be another user of Applicant's social network and may task the user with performing a specific action in order to move further within the game. By way of example and not limitation, the action may be to cut down a suspension bridge using an axe, where, in the virtual world of the RPG, the bridge extends over a gorge. Within the RPG, enemies may be following the user's avatar and the user may be given a time limit with which to cut down the bridge in order to prevent the enemies from following the user to the next phase.

To perform the task the user utilizes device 102 and, while optionally wearing additional GPS and accelerometer devices such as devices 204*a-e* around each wrist and ankle, performs movements which mimic swinging an axe to cut down the bridge. The user may even swing an actual axe and may even use the axe to cut through wood. Information regarding the user's movement and location is transmitted to a server on Applicant's network via device 102.

Once received, the server may use the information to score the user's performance. The GM may then use this score to determine whether the user's avatar was successful in cutting down the bridge in time to thwart his or her enemies. If the user was successful, the server may then generate an animation or video clip showing the bridge collapsing and the enemies falling into the gorge. Alternatively, if the user was unsuccessful, the server may generate an animation or video of the user's avatar running away from the enemies before getting to cut down the bridge.

Example V

By way of example and not limitation, two or more users may use Applicant's invention to engage in a live-action RPG together. In such an embodiment, the users' characters may be working together to achieve a common goal. As part of that goal, the server, acting as the GM, may task the users to collectively travel to another town within the RPG. To move their characters to the new town, each user may have to walk or run two miles. In certain embodiments, the server may encourage the users to perform the task together. In certain embodiments, the encouragement may be in the form of a penalty. In certain embodiments, the penalty may be an increased likelihood of a negative event, such as a character being robbed by bandits or getting lost.

To perform the task, the users may agree to meet for the two mile run. At the scheduled time, the users meet at the agreed upon location and, each carrying their own versions of device 102, such as a cellular telephone, and, in some cases, external GPS and accelerometer devices, run two miles. Information about the movement and location of each user is transmitted by their associated cellular telephones to a server on Applicant's social network. The server may use the information to determine if each individual performs the task and if the group stays together. If one person in the group falls behind because, by way of example and not limitation, that person walks the last half mile, the server may impose an additional penalty for not staying together.

While the preferred embodiments of the present invention have been illustrated in detail, it should be apparent that modifications and adaptations to those embodiments may occur to one skilled in the art without departing from the scope of the present invention.

What is claimed is:

1. A mobile communication device comprising:
   a controller comprising a processor and a non-transitory computer readable medium in communication with the processor, wherein the non-transitory computer readable medium has instructions encoded thereon to:
      record performance data that is based upon a performance of a physical activity by a user of the mobile fitness device; and
      transmit a communication comprising the performance data;
   a housing wherein the processor is located within the housing; and
   a module in communication with the processor and located external to the housing, the module being selected from the group consisting of:
      an accelerometer configured to generate movement data based upon a movement of a user of the mobile fitness device; and
      a Global Positioning System (GPS) configured to generate location data based upon a location of the user of the mobile fitness device;
   wherein the performances data comprises one of the movement data and the location data.

2. The mobile communication device of claim 1, wherein the module is an accelerometer, wherein the mobile communication device further comprises a dynamic monitoring system in communication with the accelerometer and the processor, wherein the dynamic monitoring system is configured to receive, from the accelerometer, movement data and to transmit the movement data to the processor.

3. The mobile communication device of claim 1, further comprising a wireless communication module in communication with the processor.

4. A mobile communication device comprising:
   a controller comprising a first processor, a first non-transitory computer readable medium in communication with the first processor, and computer readable program code encoded in said first non-transitory computer readable medium, the computer readable program code comprising a series of computer readable program steps to effect:
      recording performance data that is based upon a performance of a physical activity by a user of the mobile communication device; and
      transmitting a communication comprising the performance data to a server comprising a second processor and a second non-transitory computer readable medium in communication with the second processor, wherein the second non-transitory computer readable medium has instructions encoded thereon to do at least one of:

determine a score based upon the performance data; and generate a statistic based upon the performance data;

a housing wherein the processor is located within the housing; and a module in communication with the processor and located external to the housing, the module being selected from the group consisting of:

an accelerometer configured to generate movement data based upon a movement of a user of the mobile fitness device; and a Global Positioning System (GPS) configured to generate location data based upon a location of the user of the mobile fitness device;

wherein the performance data comprises one of the movement data and the location data.

5. The mobile communication device of claim 4, further comprising a wireless communication module in communication with the first processor, wherein the first non-transitory computer readable medium has instructions encoded thereon to wirelessly transmit the communication to the server, wherein the second non-transitory computer readable medium has instructions encoded thereon to wirelessly receive the communication from the mobile fitness device.

6. The mobile communication device of claim 4, wherein the second non-transitory computer readable medium further has nominal performance data encoded thereon, wherein the score is further based upon the nominal performance data, wherein the statistic is further based upon the nominal performance data.

7. A method comprising:

providing a mobile communication device comprising:

a controller comprising a processor and a non-transitory computer readable medium in communication with the processor, wherein the non-transitory computer readable medium has instructions encoded thereon to:

record performance data that is based upon a performance of a physical activity by a user of the mobile communication device; and transmit a communication comprising the performance data;

a housing wherein the processor is located within the housing; and a module in communication with the processor and located external to the housing, the module being selected from the group consisting of:

an accelerometer configured to generate movement data based upon a movement of a user of the mobile fitness device; and a Global Positioning System (GPS) configured to generate location data based upon a location of the user of the mobile fitness device;

wherein the communication further comprises one of the movement data and the location data;

generating, using the mobile communication device, the performance data; and transmitting, using the mobile communication device, the communication.

8. The method of claim 7, wherein the mobile communication device further comprises an accelerometer module in communication with the processor, wherein the accelerometer module is configured to generate movement data based upon a movement of the user of the mobile communication device, wherein the communication further comprises the movement data, the method further comprising generating, using the accelerometer module, movement data.

9. The method of claim 7, wherein the mobile communication device further comprises a Global Positioning System (GPS) module in communication with the processor, wherein the GPS module is configured to generate location data based upon a location of the user of the mobile communication device, wherein the communication further comprises the location data, the method further comprising generating, using the GPS module, location data.

10. The method of claim 7, wherein the mobile communication device further comprises a wireless communication module in communication with the processor, wherein said transmitting further comprises wirelessly transmitting, using the wireless communication module, the communication.

11. A method comprising:

providing a server comprising a processor and a non-transitory computer readable medium in communication with the processor, wherein the non-transitory computer readable medium has instructions encoded thereon to do at least one of:

determine a score based upon performance data, wherein the performance data is based upon a performance of a physical activity by a user of a mobile communication device;

generate a statistic based upon the performance data; and generate a message based upon the performance data;

receiving, using the server, a first communication comprising the performance data;

determining, using the server, at least one of:

a score based upon the performance data; and a statistic based upon the performance data;

generating the message; and posting the message to a social network.

12. The method of claim 11, wherein the non-transitory computer readable medium further has instructions encoded thereon to generate an event in a virtual game based upon the performance data, the method further comprising generating the event.

13. The method of claim 11, wherein the non-transitory computer readable medium further has instructions encoded thereon to generate a video clip based upon the performance data, the method further comprising:

generating the video clip; and posting the video clip to social network.

14. The method of claim 11, wherein the non-transitory computer readable medium further has instructions encoded thereon to generate a second communication based upon the performance data, the method further comprising:

generating the communication; and transmitting the communication to a mobile performance device.

15. The method of claim 11, wherein the non-transitory computer readable medium further has nominal performance data encoded thereon, wherein said determining further comprises calculating the score based upon the nominal performance data.

* * * * *

UNITED STATES PATENT AND TRADEMARK OFFICE
CERTIFICATE OF CORRECTION

PATENT NO.        : 8,353,770 B2                              Page 1 of 1
APPLICATION NO.   : 13/022051
DATED             : January 15, 2013
INVENTOR(S)       : Fletcher Lu It is certified that error appears in the above-identified patent and that said Letters Patent is hereby corrected as shown below:

In the Claims

Column 12, Claim 1, line 23-24, please change "mobile fitness device" to -- mobile communication device --

Column 12, Claim 1, line 33-34, please change "mobile fitness device" to -- mobile communication device --

Column 12, Claim 1, line 37, please change "mobile fitness device" to -- mobile communication device --

Column 13, Claim 4, line 10-11, please change "mobile fitness device" to -- mobile communication device --

Column 13, Claim 4, line 14, please change "mobile fitness device" to -- mobile communication device --

Column 13, Claim 5, line 24, please change "mobile fitness device" to -- mobile communication device --

Column 13, Claim 7, line 48-49, please change "mobile fitness device" to -- mobile communication device --

Column 13, Claim 7, line 52, please change "mobile fitness device" to -- mobile communication device --

Signed and Sealed this
Eighteenth Day of February, 2014

Michelle K. Lee
*Deputy Director of the United States Patent and Trademark Office*